(12) United States Patent
Twydell

(10) Patent No.: US 6,861,075 B2
(45) Date of Patent: *Mar. 1, 2005

(54) BIOCIDAL COMPOSITIONS COMPRISING AN AERATED GEL CONTAINING HYDROPHOBIC SILICA

(75) Inventor: Roland S. Twydell, Widnes (GB)

(73) Assignee: Sorex Limited, Widnes (GB)

(*) Notice: Subject to any disclaimer, the term of this patent is extended or adjusted under 35 U.S.C. 154(b) by 56 days.

This patent is subject to a terminal disclaimer.

(21) Appl. No.: 10/258,295
(22) PCT Filed: Apr. 6, 2001
(86) PCT No.: PCT/GB01/01573
§ 371 (c)(1), (2), (4) Date: Mar. 19, 2003
(87) PCT Pub. No.: WO01/80645
PCT Pub. Date: Nov. 1, 2001

(65) Prior Publication Data
US 2003/0161855 A1 Aug. 28, 2003

(30) Foreign Application Priority Data
Apr. 27, 2000 (GB) .............................. 0010149
Nov. 15, 2000 (GB) .............................. 0027834

(51) Int. Cl.⁷ .................... A01N 37/34; A01N 59/00; A01N 59/14; A01N 25/00; A01N 25/12
(52) U.S. Cl. ................. 424/613; 424/405; 424/417; 424/419; 424/489; 424/490; 424/496; 424/614; 424/615; 424/616; 424/620; 424/621; 424/622; 424/623; 424/624; 424/625; 424/626; 424/627; 424/628; 424/629; 424/657; 424/658; 424/659; 424/660; 424/724; 514/456; 514/457; 514/458; 514/521; 514/531; 514/714; 514/770; 514/772.3; 514/777; 514/782; 514/944; 514/951; 514/952; 504/150; 504/151; 504/153; 504/367

(58) Field of Search ................. 424/405, 417, 424/419, 489, 490, 496, 613–616, 620–629, 657–660, 724; 514/456–458, 521, 531, 714, 770, 772.3, 777, 782, 944, 951, 952; 504/150, 151, 153, 367

(56) References Cited

U.S. PATENT DOCUMENTS

| 3,710,510 A | 1/1973 | Tully et al. |
| 5,830,512 A | 11/1998 | Vrba |
| 6,716,885 B1 * | 4/2004 | Twydell et al. ............. 516/107 |

FOREIGN PATENT DOCUMENTS

| EP | 0 143 221 | 6/1985 |
| GB | 2 115 282 | 9/1983 |
| WO | WO 97 12516 | 4/1997 |
| WO | WO 01 35744 | 5/2001 |

* cited by examiner

Primary Examiner—John Pak
(74) Attorney, Agent, or Firm—Pearne & Gordon LLP

(57) ABSTRACT

A storage-stable biocidal aerated gel composition comprises from 30 to 97% by weight of water, from 0.2 to 5% by weight of a gelling agent selected from xanthan gum, sodium alginate and neutralised carboxyvinyl polymer from 2 to 5% by weight of a fine particulate, hydrophobic silicone-treated silica having a surface area of from 80 to 300 $m^2/g$ and from 0.004 to 20% by weight of a biocide which said composition is in the form of fine particles of an aqueous gel containing the water, gelling agent and the biocide, the surfaces of which fine particles are coated with a coating of the finely particulate hydrophobic silica. The biocidal aerated gel composition can be used to control pests using one or more appropriate biocides in the composition.

21 Claims, No Drawings

BIOCIDAL COMPOSITIONS COMPRISING AN AERATED GEL CONTAINING HYDROPHOBIC SILICA

This application is A371 of PCTGB01/01573 filed Apr. 6, 2001

The present invention relates to biocidal compositions comprising an aerated gel containing hydrophobic silica. More particularly, it relates to biocidal compositions containing hydrophobic silica, water, a biocide and a gelling agent and to a method of controlling pests using such compositions.

Aqueous dispersions of silica can be prepared into a state known generally in the prior art as "dry water". In fact, "dry water" is known in two forms. The first form can be produced by absorbing aqueous liquids onto hydrophilic material to form a material which exists as free-flowing powder or granules. The second form can be produced by coating finely divided aqueous liquids with powdered hydrophobic material, such as metal oxides. Each liquid particle in this second form of "dry water" is separated from the next by a hydrophobic metal oxide coating and by air spaces. Very high speeds of, for example, over 6000 rpm, and mixing times of 15 minutes are typically required. This second form is, however, thermodynamically unstable and, when produced, tends to break down after a relatively short period of time.

A method of controlling insects and other pests using a dry water composition containing pyrogenically produced hydrophobic silica is disclosed in U.S. Pat. No. 5,122,518. The dry water composition disclosed in the prior art, however, is unstable and cannot be stored for long periods of time. Also, when the prior art composition is applied using conventional spraying apparatus it causes blocking of the nozzles of the apparatus and cannot be sprayed over distances comparable to those achieved using a sprayable liquid.

The present invention is based on the discovery that stable aerated gels analogous to "dry water" compositions can be used for the control of pests. These stable aerated gels can be sprayed, using conventional spraying equipment, like liquids and, thus, can be sprayed over large distances without causing blocking of the nozzles of the spraying equipment.

The present invention provides a storage-stable, biocidal aerated gel composition comprising from 30 to 97% by weight of water, from 0.2 to 5% by weight of a gelling agent selected from xanthan gum, sodium alginate and neutralised carboxyvinyl polymer, from 2 to 5 by weight of a fine particulate, hydrophobic silicone-treated silica having a surface area of from 80 to 300 $m^2/g$ and from 0.004 to 20% by weight of a biocide which said composition is in the form of fine particles of an aqueous gel containing the water, gelling agent and the biocide, the surfaces of which fine particles are coated with a coating of the finely particulate hydrophobic silica.

The present invention further provides a method of controlling pests which comprises contacting the pests with a storage-stable, biocidal aerated gel composition comprising from 30 to 97% by weight of water, from 0.2 to 5% by weight of a gelling agent selected from xanthan gum, sodium alginate and neutralised carboxyvinyl polymer, from 2 to 5% by weight of a fine particulate, hydrophobic silicone-treated silica having a surface area of from 80 to 300 $m^2/g$ and from 0.004 to 20% by weight of a biocide which said composition is in the form of fine particles of an aqueous gel containing the water gelling agent and the biocide, the surfaces of which fine particles are coated with a coating of the finely particulate hydrophobic silica.

A discovery on which the present invention is based lies in the use of certain gelling agents which, when added to a premix formed by mixing the water and a specific type of hydrophobic silica under high shear conditions and then mixed with the premix also under high shear conditions, give a storage-stable aerated gel composition. Many conventional gelling agents which are ordinarily used to gel aqueous systems do not produce storage-stable gel compositions according to the present invention. The reasons for this are not, at present, understood.

Where the words "comprises" and "comprising" are used herein, it is intended that these may have the meanings "includes" and "including", respectively, to the extent that the presence of one or more other materials is not excluded.

The aerated gel composition comprises a fine particulate hydrophobic silicone-treated silica having a surface area of from 80 to 300 $m^2/g$. By the term "fine particulate", as applied to the hydrophobic silica, it is meant that the hydrophobic silica will typically have an average particle size of less than 40 $\mu$m. The silica used is one that has been rendered hydrophobic by surface treatment using one or more organosilicon compounds to produce, on the silicon dioxide surface, silicone groups. The technique of hydrophobicizing silica in this way is well-known and such silicone-treated silica is available commercially. We have found that good results are obtained by using hydrophobic silica marketed under the name CAB-O-SIL ("CAB-O-SIL" is a trademark of Cabot Corporation), preferably CAB-O-SIL TS720. However, other silicone-treated silicas can also be used in the present invention if they have a surface area within the range of from 80 to 300 $m^2/g$. The hydrophobic silica may also be one that has been surface treated to produce siloxane, as well as, silicone groups attached to the silicon dioxide surface.

The hydrophobic silica is used in an amount of from 2 to 5% by weight based on the total weight of the composition. The use of greater than 5% by weight of the hydrophobic silica results in a gel composition which is excessively dusty. The use of such a composition may give rise to a greater nuisance dust risk. Preferably, the amount of hydrophobic silica will be in the range of from 3 to 5%, and more preferably from 3 to 4%, by weight of the composition.

The water used may typically be tap water although purified grades may be appropriate for some applications. The water will normally be used at ambient temperature since there appears to be no advantage in using heated or cooled water in the performance of the invention. The water generally will form from 30 to 97% by weight of the total composition. Typically, however, the amount of water will be in the range of from 80 to 97% by weight to ensure the formation of aerated gel compositions of good consistency and improved stability. Preferably, however, the amount of water will be in the range of 85 to 97% by weight of the final composition. The amount of water used to prepare a particular biocidal composition of the invention will typically depend on the solubility of the biocide incorporated into the composition. For instance, in the case of a hydrophilic biocide the amount of water used will preferably be within the range of from 85 to 97% by weight of the composition. However, if the biocide is hydrophobic the amount of water used preferably comprises at least 90% by weight of the composition. The use of a higher water content, in the case of hydrophobic biocides, not only facilitates the incorporation of the biocide into the aqueous gel but facilitates a homogeneous distribution of the biocide in the fine particles of the aqueous gel.

As mentioned above, the gelling agent is one or more selected from xanthan gum, sodium alginate and neutralised carboxyvinyl polymers, such as carboxypolymethylene neutralised with triethanolamine. These gelling agents are included in an amount of from 0.2 to 5% by weight. The use of an amount greater than 5% by weight of the gelling agent results in a gel composition having an excessively high gel strength. Preferably, from 0.5% to 2% by weight of the gelling agent will be used depending on the desired stability and structure of the gel composition. We have produced biocidal storage-stable aerated gels, having good properties using less than 1% by weight of gelling agent based on the weight of the final composition. Other hydrophilic or hydrophobic additives known to those skilled in the art may be incorporated to modify the physical or biological properties of the composition. Examples of additives include flavourants, perfumes, attractants, stabilisers and detergents.

The biocide which, according to the present invention, is incorporated into the aerated gel composition may comprise one or more biocidally-active compounds. We have previously found that aerated gel compositions containing hydrophobic silica have biocidal activity in the absence of any added biocide, for instance insecticidal and acaricidal activity of such aerated gel compositions have been noted. The incorporation of a biocide into the aerated gel compositions, however, extends the spectrum of biocidal activity that can be obtained depending on the choice of biocide used. The biocide may, for instance, be selected from one or more rodenticides, insecticides and microbicides. The biocide may be hydrophilic or hydrophobic. Examples of biocides that can be used in the present invention include, but are not limited to, rodenticides of the coumarin-type such as difenacoum, insecticides such as boric acid and pyrethroids, e.g., cypermethrin and d-phenothrin and microbicides, such as peroxygen compounds.

The amount of biocide incorporated into the aerated gel composition of the present invention is in the range of from 0.004 to 20% by weight based on the weight of the composition. The inclusion level will obviously depend on the potency of the biocide used and the desired biological performance of the composition. Typically, the biocide will be used in an amount to give a final biocide content in the composition of from 0.005 to 10% by weight based on the weight of the composition. The composition may further contain one or more compounds which stabilise the biocide or act as an adjuvant for the biocide.

The process for producing the gel compositions involves mixing the water with the biocide and the silica under high shear conditions typically for a few minutes, for example 2 to 5 minutes. The mixing at this stage in the process must be carried out under high shear conditions, i.e., conditions that cause the water to be finely fragmented into minute droplets which become dispersed within the finely particulate hydrophobic silica such that the surfaces of the water droplets become coated with the hydrophobic silica particles. The term "high shear" is, of course, well-known to the person skilled in the art of mixing or blending and whether or not a particular mixing apparatus is capable of mixing aqueous compositions under high shear conditions will be known to one skilled in the art. This may be achieved by using standard high speed mixers, typically using a mixing speed of at least 1500 rpm and generally from 2000 to 6000 rpm. When the biocide used is hydrophilic we have found that it is preferable to dissolve the biocide into the water and then to mix the solution of biocide with the hydrophobic silica to partially disperse the silica into the solution. By incorporating the biocide in this way a homogenous distribution of the biocide throughout the eventual gel product can be obtained. However, when the biocide used is hydrophobic we prefer to mix the water, the hydrophobic silica and the hydrophobic biocide together under high shear conditions to partially disperse the silica with the biocide and the water. If the biocide is, itself, a solid material, then it is preferred to add this as a solution in a minimum amount of an organic solvent with the water and hydrophobic silica in order to facilitate the eventual production of an aerated gel having a homogeneous distribution of the biocide. After the hydrophobic silica the water and the biocide have been mixed to create a dispersion of fine droplets of aqueous phase in the silica, the gelling agent is added and mixing at high speed, typically at high shear conditions, is continued for several minutes until the gelling agent has been thoroughly incorporated into the aqueous phase. It is preferred in the present invention to add the gelling agent after the silica, water and biocide have been thoroughly mixed together. If the gelling agent is added before the silica, mixing requires more energy and the homogeneity and stability of the resulting gel composition can be compromised.

The aerated gel compositions of the present invention, by choice of one or more appropriate biocides, can be tailored to have activity against a variety of pests. For instance, the product aerated gel composition can be used as a rodenticidal contact formulation by incorporating a rodenticide such as a difenacoum into the composition. Ant bait formulations can be obtained by using, as the biocide in the aerated gel composition, an effective amount of boric acid. According to a preferred embodiment, the aerated gel composition of the invention contains as biocide, an insecticide which is effective for the control of wasp nests, e.g., nests of the common wasp, *Vespula vulgaris* and the tree wasp, *Dolichovespula sylvestris*. An example of a wasp nest control formulation comprises an aerated gel composition of the invention containing, as biocide, the insecticide d-phenothrin in an effective amount.

Although we do not wish to be bound by theory, we believe that the aerated gel composition is particularly effective against pests because of the tendency of the composition to stick to the body of the pest. In the case of insects, the composition can stick to the legs and can render the insect immobile. The silica in the composition also has insecticidal activity as it physically removes epicuticular wax from the insect resulting in the loss of hydrostatic stability.

The aerated gel compositions are properly sprayable like liquids using conventional spraying equipment, unlike known pulverulent dry water compositions. The compositions do not normally cause any blocking of nozzles in the spraying equipment unlike known pulverulent dry water compositions although in the event that any blocking does occur the equipment can simply be washed with water, e.g., tap water, to remove the blockage. The water content of the aerated gel composition makes it possible to spray the composition with intended direction, over large distances and enables the composition, when sprayed, to stick to the target. This property is particularly useful when a composition is used as a wasp control formulation for spraying into the wasp nest. Contrariwise, pulverulent solid compositions cannot be sprayed far or with any great degree of direction and are less likely to stick to the target.

The storage-stable compositions of the present invention are free-flowing, pulverulent fluids and can be used in formulations produced for domestic, veterinary, agricultural and horticultural applications.

The invention will now be illustrated by the following examples in which the compositions in Examples 1 to 11 were mixed using an IKA RE166 high speed mixer having a radial flow toothed disc mixer head and the composition in Example 12 was mixed using a larger scale Torrance high speed mixer having a radial flow toothed disc mixer head.

EXAMPLE 1

A hydrophilic solution of 0.5% by weight difenacoum rodenticide in triethanolamine and glycol 1 g, was mixed with tapwater 95.5 g at 1500 rpm for 2 minutes. CAB-O-SIL TS720 (silica) 3 g was added and mixing continued at 2800 rpm for 5 minutes. Powdered xanthan gum 0.5 g was added and the mixer speed increased to 5500 rpm for a further 5 minutes. A free-flowing aerated gel was formed with a density of 0.5 g/ml. Analysis of the gel showed 0.0048% by weight difenacoum. A subsample of the gel left to dry at ambient for 2 days lost 95.5% by weight of its original weight. Analysis of the dried subsample showed 0.1192% by weight difenacoum. This level of difenacoum is appropriate for use as a rodentical contact formulation.

EXAMPLE 2

A hydrophilic peroxygen disinfectant, SORGENE 5 (Sorex Limited) 1 g was mixed with tapwater 95.5 g at 1500 rpm for 2 minutes. CAB-O-SIL TS720 (silica) 3 g was added and mixing continued at 2800 rpm for 5 minutes. Powdered xanthan gum 0.5 g was added and the mixer speed increased to 5500 rpm for a further 5 minutes. A free-flowing aerated gel was formed with a density of 0.5 g/ml.

EXAMPLE 3

A water soluble insecticide, boric acid, 4 g and granulated sucrose 7 g were dissolved in tapwater 85.5 g at 1500 rpm for 5 minutes. CAB-O-SIL TS720 (silica) 3 g, was added and mixing continued at 2800 rpm for 5 minutes. Powdered xanthan gum 0.5 g was added and the mixer speed increased to 5500 rpm for a further 5 minutes. A free-flowing aerated gel was formed with a density of 0.5 g/ml. This level of boric acid is appropriate for an ant bait formulation.

EXAMPLE 4

A water soluble insecticide, boric acid, 1 g and a flavour vanillin 0.05 g were dissolved in tapwater 95.45 g at 1500 rpm for 5 minutes. CAB-O-SIL TS720 (silica) 3 g, was added and mixing continued at 2800 rpm for 5 minutes. Powdered xanthan gum 0.5 g, was added and the mixer speed increased to 5500 rpm for a further 5 minutes. A free-flowing aerated gel was formed with a density of 0.5 g/ml. This level of boric acid and vanillin is appropriate for an ant bait formulation. A sample of this formulation was kept under ambient conditions for a period of 17 months. Analysis after this storage period showed the sample still to be stable and not to have undergone separation of components.

EXAMPLE 5

The hydrophobic solid pyrethroid, cypermethrin 2 g, was dissolved in di-isodecyl phthalate 8 g. This solution 1 g, was mixed with tapwater 95.5 g and CAB-O-SIL TS720 (silica) 3 g at 2800 rpm for 5 minutes. Powdered xanthan gum 0.5 g was added and the mixer speed increased to 5500 rpm for a further 5 minutes. A free-flowing aerated gel was formed. Analysis showed 0.16% by weight cypermethrin. Adults and larvae of the litter beetle, *Alphitobius diaperinus*, were exposed to a dried deposit of this gel for 5 seconds and then transferred to a clean container. Ten individuals were tested for each stage. Total knockdown occurred within 10 minutes of exposure with both stages.

EXAMPLE 6

The hydrophobic solid pyrethroid, bifenthrin 0.06 g, was dissolved in dioctyl adipate 0.54 g. This solution was mixed with tapwater 95.9 g and CAB-O-SIL TS720 (silica) 3 g at 2800 rpm for 5 minutes. Powdered xanthan gum 0.5 g was added and the mixer speed increased to 5500 rpm for a further 5 minutes. A free-flowing aerated dry gel was formed. Worker termites, *Reticulitermes santonensis*, were continuously exposed to a dried deposit of this formulation on filter paper. Total knockdown occurred within 45 minutes of exposure and complete mortality was obtained within 24 hours. Adult poultry red mites, *Dermanyssus gallinea*, were continually exposed to a dry deposit of this formulation on filter paper. Mites were unable to walk within 30 seconds of contact. There was 70% mortality within 1 hour and complete mortality within 2 hours.

EXAMPLE 7

The hydrophobic liquid pyrethroid, d-phenothrin 4 g, was mixed with tapwater 964 g and CAB-O-SIL TS720 30 g at 2800 rpm for 5 minutes. Powdered xanthan gum 2 g, was added and the mixer speed increased to 5500 rpm for a further 5 minutes. A free-flowing aerated gel was formed. This gel was applied as a wet dust through a BIRCHMEIR DR5 duster fitted with a 4.5 m lance extension without blockage. Analysis of the gel showed 0.4% by weight d-phenothrin. Two accelerated storage tests were conducted on bottled subsamples, one cycling the gel from −20 to +20° C., the other storing the gel at 54° C. After 5 days there was 40% by weight separation in the cycled subsample and 20% by weight separation in the subsample at 54° C. Both subsamples were easily re-homogenised by 3 inversions.

EXAMPLE 8

The hydrophobic liquid pyrethroid, d-phenothrin 0.4 g was mixed with tapwater 95.6 g and CAB-O-SIL TS720 3.5 g at 2800 rpm for 5 minutes. Powdered xanthan gum 0.5 g was added and the mixer speed increased to 5500 rpm for a further 5 minutes. A free-flowing aerated gel was formed with a density of 0.5 g/ml. This gel was dustier in appearance then the formulation produced according to Example 7 above.

EXAMPLE 9

The hydrophobic liquid pyrethroid, d-phenothrin 0.4 g was mixed with tapwater 95.2 g and CAB-O-SIL TS720 4 g at 2800 rpm for 5 minutes. Powdered xanthan gum 0.4 g was added and the mixer speed increased to 5500 rpm for a further 5 minutes. A free-flowing aerated gel was formed with a density of 0.6 g/ml. This gel was dustier in appearance than that produced according to Example 8 above.

EXAMPLE 10

The hydrophobic liquid pyrethroid, d-phenothrin 8 g, was mixed with tapwater 1,882 g and CAB-O-SIL TS720 10 g at 5000 rpm for 5 minutes. Powdered xanthan gum 10 g was added and the mixer speed increased to 5500 rpm for a further 5 minutes. A free-flowing aerated gel was formed with a density of 0.6 g/ml. Analysis showed 0.39% by weight d-phenothrin. This gel was dustier in appearance than that produced in Example 9. A subsample of this gel was applied by a BIRCHMEIR DR5 duster to an active wasp nest, *Vespula vulgaris*, in the ground. The nest entrance was applied with 350 g of the gel. The wasps did not respond aggressively to the application. All wasp activity ceased within 7 days from application.

EXAMPLE 11

The hydrophobic liquid pyrethroid, d-phenothrin 4 g was mixed with tapwater 961 g and CAB-O-SIL TS720 30 g at 5000 rpm for 5 minutes. Powdered xanthan gum 5 g was added and the mixer speed increased to 5500 rpm for a further 10 minutes. A free-flowing aerated gel was formed with a density of 0.6 g/ml. Initial analysis showed 0.43% by weight d-phenothrin. Two accelerated storage tests were conducted on bottled subsamples, one cycling the gel from −20° C. to +20° C., the other storing the gel at 54° C. After 14 days there was no water separation in either subsample. Analysis after storage showed 0.42% by weight d-phenothrin for the cycled subsample and 0.48% by weight d-phenothrin for the subsample at 54° C. The remainder of the gel was stored at ambient. Analysis of the ambient sample after 12 months showed 0.39% by weight d-phenothrin.

EXAMPLE 12

The hydrophobic liquid pyrethroid, d-phenothrin 0.2 kg was mixed with tapwater 48.05 kg and CAB-O-SIL TS720 1.5 kg at 2500 rpm for 5 minutes. Powdered xanthan gum 0.25 kg was added and mixing continued at the same speed for a further 10 minutes. A free-flowing aerated gel was formed with a density of 0.6 g/ml. Analysis showed 0.42% by weight d-phenothrin. Four active wasp nests were applied with this gel using a BIRCHMEIR DR5 duster. Two of the nests were of the common wasp, *Vespula vulgaris* in house lofts and one of the same species in the ground. The fourth nest was of a tree wasp *Dolichovespula sylvestris* on the outside of a porch. Each application was made to the inside of the nest either through the nest entrance or through the nest wall. The quantity of gel applied ranged from 85 to 750 g depending on the size of the nest. None of the wasps reacted aggressively to application. On all nests wasp activity ceased within 1 day from application.

Adult houseflies, *Musca domestica*, were exposed to a deposit from a 24 month old sample of this formulation freshly applied to filter paper. Total knockdown occurred within 1.5 minutes. There was complete mortality within 24 hours.

What is claimed is:

1. A storage-stable biocidal aerated gel composition comprising from 30 to 97% by weight of water, from 0.2 to 5% by weight of a gelling agent selected from the group consisting of xanthan gum, sodium alginate and neutralised carboxyvinyl polymer, from 2 to 5% by weight of a fine particulate, hydrophobic silicone-treated silica having a surface area of from 80 to 300 $m^2/g$, and from 0.004 to 20% by weight of a biocide, which said composition is in the form of fine particles of an aqueous gel containing the water, gelling agent and the biocide, the surfaces of which fine particles are coated with a coating of the finely particulate hydrophobic silica.

2. A composition according to claim 1, comprising from 85 to 97% by weight of water.

3. A composition according to claim 2, comprising from 3 to 5% by weight of the silica.

4. A composition according to claim 2, wherein the gelling agent is xanthan gum.

5. A composition according to claim 2, wherein the biocide is selected from the group consisting of a rodenticide, an insecticide, a microbiocide and an acaricide.

6. A composition according to claim 1, comprising from 3 to 5% by weight of the silica.

7. A composition according to claim 6, wherein the gelling agent is xanthan gum.

8. A composition according to claim 6, wherein the biocide is selected from the group consisting of a rodenticide, an insecticide, a microbiocide and an acaricide.

9. A composition according to claim 1, wherein the gelling agent is xanthan gum.

10. A composition according to claim 9, wherein the biocide is selected from the group consisting of a rodenticide, an insecticide, a microbiocide and an acaricide.

11. A composition according to claim 1, wherein the biocide is selected from the group consisting of a rodenticide, an insecticide, a microbiocide and an acaricide.

12. A composition according to claim 11, wherein the biocide is difenacoum.

13. A composition according to claim 11, wherein the biocide is selected from the group consisting of boric acid, cypermethrin and d-phenothrin.

14. A composition according to claim 11, wherein the biocide is a stabilised blend of peroxygen compounds.

15. A method of controlling rodents which comprises contacting the rodents with a composition according to claim 12.

16. A method of controlling insects which comprises contacting the insects with a composition according to claim 13.

17. A method according to claim 16, wherein the insects are wasps.

18. A method of preparing a storage-stable, particulate, biocidal aerated gel composition comprising mixing from 30 to 97% by weight water, from 0.004 to 20% by weight of a biocide and from 2 to 5% by weight of a fine particulate hydrophobic, silicone-treated silica having a surface area of 80 to 300 $m^2/g$ under high shear conditions to produce a dispersion, adding to the dispersion from 0.2 to 5% by weight of a gelling agent selected from the group consisting of xanthan gum, sodium alginate and neutralised carboxyvinyl polymer and mixing the composition under high shear conditions to produce fine particles of an aqueous gel, the surfaces of which are coated with a coating of finely particulate hydrophobic silica.

19. A method according to claim 18, wherein a soluble biocide is dissolved in the water before the fine particulate hydrophobic silica is mixed with the water under high shear conditions.

20. A method according to claim 18, wherein a hydrophobic biocide is mixed together with the water and the fine particulate hydrophobic silica.

21. A method according to claim 18, wherein a solid hydrophobic biocide is first dissolved in an organic solvent and the solution obtained is then mixed with the water and the hydrophobic silica under high shear conditions prior to the addition of the gelling agent.

* * * * *